(12) United States Patent
Pugh et al.

(10) Patent No.: US 9,375,885 B2
(45) Date of Patent: *Jun. 28, 2016

(54) PROCESSOR CONTROLLED OPHTHALMIC DEVICE

(75) Inventors: Randall B. Pugh, Jacksonville, FL (US); Daniel B. Otts, Jacksonville, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,720

(22) Filed: Oct. 14, 2009

(65) Prior Publication Data

US 2010/0109175 A1  May 6, 2010

Related U.S. Application Data

(60) Provisional application No. 61/110,213, filed on Oct. 31, 2008.

(51) Int. Cl.
*B29D 11/00* (2006.01)
*G02C 7/04* (2006.01)
*A61F 2/14* (2006.01)

(52) U.S. Cl.
CPC .......... *B29D 11/00038* (2013.01); *A61F 2/14* (2013.01); *B29D 11/00028* (2013.01); *B29D 11/00826* (2013.01); *G02C 7/04* (2013.01)

(58) Field of Classification Search
USPC .......... 264/1.1, 1.7, 1.36, 1.38; 425/135, 162, 425/163, 808

IPC ..... B29D 11/00028,11/00826, 11/00038; G02C 7/04; A61F 2/14

See application file for complete search history.

(56) References Cited

U.S. PATENT DOCUMENTS

| | | | |
|---|---|---|---|
| 4,075,420 A | 2/1978 | Walton | |
| 5,143,660 A | 9/1992 | Hamilton | |
| 5,573,108 A | 11/1996 | Hamilton | |
| 5,578,332 A | 11/1996 | Hamilton | |
| 6,071,440 A * | 6/2000 | Wang et al. | 264/1.1 |
| 6,609,041 B1 | 8/2003 | Sanka et al. | |
| 6,834,955 B2 | 12/2004 | Doshi | |
| 6,986,579 B2 * | 1/2006 | Blum et al. | 351/159.39 |
| 7,612,948 B2 * | 11/2009 | Immink et al. | 359/666 |
| 7,931,832 B2 * | 4/2011 | Pugh et al. | 264/1.32 |
| 8,043,370 B2 | 10/2011 | Bretthauer et al. | |
| 8,080,187 B2 * | 12/2011 | Tepedino et al. | 264/1.32 |

(Continued)

FOREIGN PATENT DOCUMENTS

| | | |
|---|---|---|
| CN | 1719998 A | 1/2006 |
| EP | 367513 A2 | 5/1990 |

(Continued)

OTHER PUBLICATIONS

PCT International Search Report dated Jan. 28, 2010 for PCT Intl. Appln. No. PCT/US2009/061780.

(Continued)

*Primary Examiner* — Mathieu Vargot

(57) ABSTRACT

This invention discloses methods and apparatus for providing a media insert with a Data Processor into an ophthalmic lens. An energy source is capable of powering the Data Processor included within the ophthalmic lens. In some embodiments, an ophthalmic lens is cast molded from a silicone hydrogel.

6 Claims, 7 Drawing Sheets

(56) References Cited

U.S. PATENT DOCUMENTS

| | | | |
|---|---|---|---|
| 2004/0051190 A1* | 3/2004 | Slack et al. | 264/2.5 |
| 2005/0099594 A1* | 5/2005 | Blum et al. | 351/160 R |
| 2006/0126698 A1 | 6/2006 | Blum | |
| 2006/0181676 A1 | 8/2006 | Tucker et al. | |
| 2008/0099515 A1 | 5/2008 | Szuch | |
| 2008/0101267 A1 | 5/2008 | Kurokawa | |
| 2009/0105817 A1 | 4/2009 | Bretthauer et al. | |
| 2009/0202709 A1 | 8/2009 | Szuch | |
| 2010/0109175 A1 | 5/2010 | Pugh et al. | |

FOREIGN PATENT DOCUMENTS

| | | |
|---|---|---|
| EP | 367513 A3 | 4/1991 |
| EP | 561480 A2 | 9/1993 |
| EP | 561481 A2 | 9/1993 |
| EP | 561480 A3 | 10/1993 |
| EP | 561481 A3 | 10/1993 |
| EP | 367513 B1 | 7/1995 |
| EP | 561481 B1 | 1/1997 |
| EP | 561480 B1 | 8/1997 |
| EP | 1818692 A2 | 8/2007 |
| EP | 1897668 A1 | 3/2008 |
| EP | 1 262 307 B1 | 2/2010 |
| JP | 6-165570 | 6/1994 |
| JP | 2007526517 | 9/2005 |
| JP | 2008-505421 | 10/2006 |
| JP | 2008135 018 | 10/2007 |
| JP | 2008-93659 | 4/2008 |
| JP | 2008-135018 | 6/2008 |
| TW | 201029830 | 8/2010 |
| WO | WO 03091785 | 11/2003 |
| WO | WO 2004015460 | 2/2004 |
| WO | WO 2004049927 | 6/2004 |
| WO | WO 2005016617 | 2/2005 |
| WO | WO 2005/088388 * | 9/2005 |
| WO | WO 2006004973 | 1/2006 |
| WO | WO 2006137903 | 12/2006 |
| WO | WO 2007020184 | 2/2007 |
| WO | WO 2008053789 | 5/2008 |
| WO | WO 2008091859 A1 | 7/2008 |

OTHER PUBLICATIONS

Russian Reporting Letter dated Aug. 15, 2013 for corresponding Patent Application No. 2011121846.

* cited by examiner

```
┌─────────────────────────────────────┐
│  PLACE A MEDIA INSERT COMPRISING A DATA  │
│    PROCESSOR AND AN ENERGY SOURCE   │
│       WITHIN AN OPHTHALMIC LENS     │
│                                 501 │
└─────────────────────────────────────┘
                   │
┌─────────────────────────────────────┐
│  PLACE THE ENERGY SOURCE IN ELECTRICAL  │
│      COMMUNICATION WITH THE DATA    │
│              PROCESSOR              │
│                                 502 │
└─────────────────────────────────────┘
                   │
┌─────────────────────────────────────┐
│    DIRECT ELECTRICAL CURRENT THROUGH    │
│          THE DATA PROCESSOR         │
│                                 503 │
└─────────────────────────────────────┘
                   │
┌─────────────────────────────────────┐
│     OPERATE THE DATA PROCESSOR TO   │
│   GENERATE A COMMAND TO CHANGE THE  │
│  STATE OF AT LEAST ONE COMPONENT IN │
│              THE LENS           504 │
└─────────────────────────────────────┘
```

FIG. 5

PROCESSOR CONTROLLED OPHTHALMIC DEVICE

CROSS REFERENCE TO RELATED APPLICATIONS

The present invention claims priority to the U.S. Provisional Application No. 61/110,213 entitled Processor Controlled Ophthalmic Device, filed Oct. 31, 2008, the contents of which are relied upon and incorporated herein.

FIELD OF USE

The present invention describes an ophthalmic device including a data processing device, and more specifically, methods of fabrication of an ophthalmic lens with a media insert embedding a data processor and one or more components.

BACKGROUND

Traditionally an ophthalmic lens, such as a contact lens or an intraocular lens provided a predetermined optical quality. A contact lens, for example, can provide one or more of: vision correcting functionality; cosmetic enhancement; and therapeutic effects, but only a set of vision correction functions. Each function is provided by a physical characteristic of the lens. Basically a design incorporating a refractive quality into a lens provides vision corrective functionality. A pigment incorporated into the lens can provide a cosmetic enhancement. An active agent incorporated into a lens can provide a therapeutic functionality.

To date optical quality in an ophthalmic lens has been designed into the physical characteristic of the lens. Generally, an optical design has been determined and then imparted into the lens during fabrication of the lens, such as, for example through cast molding, or lathing. The optical qualities of the lens have remained static once the lens has been formed. However, wearers may at times find it beneficial to have more than one focal power available to them in order to provide sight accommodation. Unlike spectacle wearers, who can change spectacles to change an optical correction, contact wearers or those with intraocular lenses have not been able to change the functional characteristics of their vision correction without significant effort.

SUMMARY

Accordingly, the present invention includes an ophthalmic lens with a data processor which is operative to change a state of one or more components within an ophthalmic lens. A change in state of a component may provide additional functionality by the ophthalmic lens. In addition, methods and apparatus for forming an ophthalmic lens, with data processor are presented. Some embodiments can also include a cast molded silicone hydrogel contact lens with a rigid or formable energized insert which additionally includes a data processor, wherein the insert is included within the ophthalmic lens in a biocompatible fashion.

Generally, a processor and an energy source can be attached to or made a part of a media insert and the media insert is placed proximate to at least one of a first mold part and a second mold part. A reactive monomer mix is additionally placed between the first mold part and the second mold part. The first mold part is positioned proximate to the second mold part thereby forming a lens cavity with the energized media insert and at least some of the reactive monomer mix in the lens cavity; the reactive monomer mix is exposed to actinic radiation to form an ophthalmic lens. A lens is formed via control of the actinic radiation to which the reactive monomer mixture is exposed. The media insert with the data processor is included within the lens.

DESCRIPTION OF THE DRAWINGS

FIG. 5 illustrates method steps according to some additional aspect of the present invention.

DETAILED DESCRIPTION OF THE INVENTION

Figure 1:
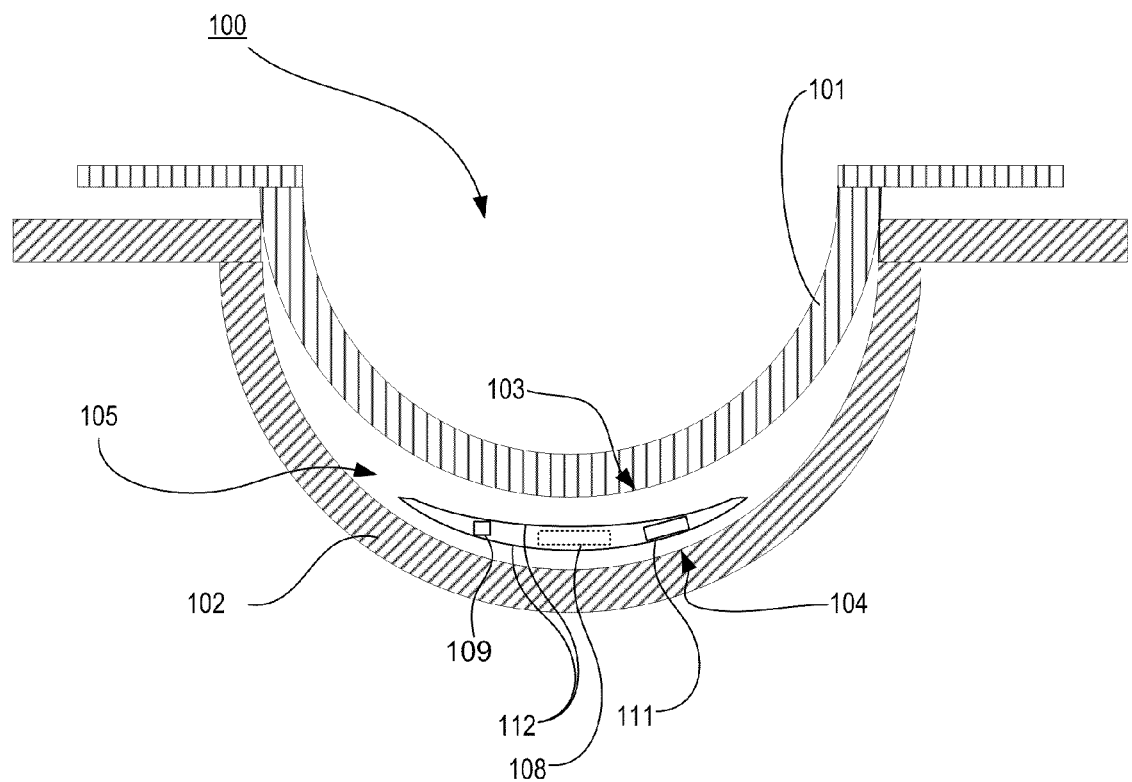
FIG. 1 illustrates a mold assembly apparatus according to some embodiments of the present invention.

The present invention includes methods and apparatus for manufacturing an ophthalmic lens with a data processor. In addition, the present invention includes an ophthalmic lens with a data processor incorporated into the ophthalmic lens.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Data Processor: as used herein refers to a circuit or series of circuits capable of receiving digital data and performing a calculation based upon the data received.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to a device capable of supplying Energy or placing a biomedical device in an Energized state.

Energy Harvesters: as used herein refers to a device capable of extracting energy from an environment and converting the extracted energy to electrical energy.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Lens forming mixture or "Reactive Mixture" or "RMM" (reactive monomer mixture): as used herein refers to a monomer or prepolymer material which can be cured and crosslinked or crosslinked to form an ophthalmic lens. Various embodiments can include lens forming mixtures with one or more additives such as: UV blockers, tints, photoinitiators or catalysts, and other additives one might desire in an ophthalmic lens such as, contact or intraocular lenses.

Lens Forming Surface: refers to a surface that is used to mold a lens. In some embodiments, any such surface 103-104 can have an optical quality surface finish, which indicates that it is sufficiently smooth and formed so that a lens surface fashioned by the polymerization of a lens forming material in contact with the molding surface is optically acceptable. Further, in some embodiments, the lens forming surface 103-104 can have a geometry that is necessary to impart to the lens surface the desired optical characteristics, including without limitation, spherical, aspherical and cylinder power, wave front aberration correction, corneal topography correction and the like as well as any combinations thereof.

Lithium Ion Cell: refers to an electrochemical cell where Lithium ions move through the cell to generate electrical energy. This electrochemical cell, typically called a battery, may be reenergized or recharged in its typical forms.

Media Insert: as used herein refers to a formable or rigid substrate capable of supporting an Energy Source within an ophthalmic lens. In some embodiments, the Media Insert also includes one or more variable optic lenses.

Mold: refers to a rigid or semi-rigid object that may be used to form lenses from uncured formulations. Some preferred molds include two mold parts forming a front curve mold part and a back curve mold part.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate for a certain, reestablished time period.

Reenergize or Recharge: To restore to a state with higher capacity to do work. Many uses within this invention may relate to restoring a device to the capability to flow electrical current at a certain rate for a certain, reestablished time period.

Released from a mold: means that a lens is either completely separated from the mold, or is only loosely attached so that it can be removed with mild agitation or pushed off with a swab.

Referring now to FIG. 1, an ophthalmic lens 100 with an embedded Data Processor 111 may also include an Energy Source 109, such as an electrochemical cell or battery as the storage means for the energy and in some embodiments, encapsulation and isolation of the materials comprising the Energy Source from an environment into which an ophthalmic lens is placed. The Energy Source 109 can provide power to activate the data processor.

A diagram of an exemplary assembly mold 100 for an ophthalmic lens is illustrated with a Data Processor 111. A mold includes an assembly mold 100 having a cavity 105 into which a lens forming mixture can be dispensed such that upon reaction or cure of the lens forming mixture, an ophthalmic lens of a desired shape is produced. The molds and mold assemblies 100 of this invention are made up of more than one "mold parts" or "mold pieces" 101-102. The mold parts 101-102 can be brought together such that a cavity 105 is formed between mold parts 101-102 in which a lens can be formed. This combination of mold parts 101-102 is preferably temporary. Upon formation of the lens, the mold parts 101-102 can again be separated for removal of the lens.

At least one mold part 101-102 has at least a portion of its surface 103-104 in contact with the lens forming mixture such that upon reaction or cure of the lens forming mixture that surface 103-104 provides a desired shape and form to the portion of the lens with which it is in contact. The same is true of at least one other mold part 101-102.

Thus, for example, in a preferred embodiment a mold assembly 100 is formed from two parts 101-102, a female concave piece (front piece) 102 and a male convex piece (back piece) 101 with a cavity formed between them. The portion of the concave surface 104 which makes contact with lens forming mixture has the curvature of the front curve of an ophthalmic lens to be produced in the mold assembly 100 and is sufficiently smooth and formed such that the surface of an ophthalmic lens formed by polymerization of the lens forming mixture which is in contact with the concave surface 104 is optically acceptable.

A lens forming surface can include a surface 103-104 with an optical quality surface finish, which indicates that it is sufficiently smooth and formed so that a lens surface fashioned by the polymerization of a lens forming material in contact with the molding surface is optically acceptable. Further, in some embodiments, the lens forming surface 103-104 can have a geometry that is necessary to impart to the lens surface any desired optical characteristics, including without limitation, spherical, aspherical and cylinder power, wave front aberration correction, corneal topography correction and the like as well as any combinations thereof. According to the present invention, optical characteristics can work in concert with a Data Processor 111 to provide an overall optical quality.

A data processor can provide manipulation of data from within the confines of an ophthalmic lens. In some embodiments, the manipulation of data can include generating one or more instructions based upon data received. In some embodiments, the received data can be indicative of a condition proximate to the lens, such as, for example: an amount of moisture to which the lens is exposed, a temperature of a lens surface, a state of an electrowetted device included within the lens, or other condition.

Additional embodiments may include a state of a component included within a lens such as the status of a counter used to time a supply of power to a component or an input received by a component. An input received can include, for example, a magnetic pulse, a light pattern, a radio frequency signal or other form of data communication.

Some additional embodiments can also include the data processor issuing a command to change a state of a liquid meniscus lens portion 108 within an ophthalmic lens; wherein the change of state of the liquid meniscus lens portion changes the optical qualities of the lens.

An instruction generated can include a command to control a component included within the ophthalmic lens or a command to transmit data from the ophthalmic lens. By way of non-limiting example, a command to control a component included within the ophthalmic lens can include: a predetermined polling cycle of receipt of an external signal to activate one or more components contained within the ophthalmic lens. In order to improve efficiency of some components, such as a magnetic sensing switch or a photoreceptor functioning as an activation switch, a processor can be programmed to cause the component to turn on at specific intervals. In this manner, for example the magnetic sensing switch may only consume energy for 10 seconds (or some other interval) each minute of time. Other embodiments, may cause the Data Processor to receive input from a component sensing temperature of a lens; surface tension of a lens; pressure on a lens; or other parameter which is measurable by an electronic, electromechanical or MEMs device.

A Data Processor 111 can include, by way of non-limiting example, an ultra-low power microcontroller 16 bit or 32 bit RISC mixed signal processor. Preferably the data processor will be sealed, such as hermetically sealed in a ceramic or other impervious material. The power consumption is preferably low, such as 250 micro amps/MIPS active. One example includes the Texas Instruments MSP 430 microprocessor.

In some additional embodiments, the Data Processor can issue commands to control a variable focal length lens. The controls can cause an electrical current to be applied across two or more transparent borders that generally parallel delimit an internal volume containing two non-miscible liquids. The two non-miscible liquids will have different optical indices. An elastic element is positioned such that it will deform in response to a change in pressure of the liquids. The pressure of the liquids changes in response to changes that the instructions from the Data Processor cause in the electrical charge placed across one or both of the liquids.

In some embodiments a Data Processor 111 controlled variable lens can include a liquid meniscus lens including a liquid containing cell for retaining a volume of two or more liquids. A lower surface, which is non-planar, includes a conical or cylindrical depression or recess, of axis delta, which contains a drop of an insulating liquid. A remainder of the cell includes an electrically conductive liquid, non-miscible with the insulating liquid, having a different refractive index and, in some embodiments a similar or same density. An annular electrode, which is open facing a recess, is positioned on the rear face of a lower plate. Another electrode is placed in contact with the conductive liquid. Application of a voltage across the electrodes is utilized to create electrowetting and modify the curvature of the interface between the two liquids, according to the voltage (V) applied between the electrodes. A beam of light passing through the cell normal to the upper plate and the lower plate and in the region of the drop will be focused to a greater or lesser extent according to the voltage applied to the electrodes. The conductive liquid is typically an aqueous liquid, and the insulating liquid is typically an oily liquid.

A user controlled adjustment device can be used to interface with the Data Processor and thereby control the focus of the lens. The adjustment device can include, by way of non-limiting example, a magnetically activated switch, a photo-optically activated switch, an electrical sensor sensing a signal within the eye to focus, a radio frequency transmission device or any other electronic device or passive device for providing a user supplied instruction to the processor.

In some embodiments, a lens with a Data Processor 111 placed on a media, which includes a rigid center soft skirt design in which a central rigid optical element including the Data Processor 111 is in direct contact with the atmosphere and the corneal surface on respective an anterior and posterior surfaces, wherein the soft skirt of lens material (typically a hydrogel material) is attached to a periphery of the rigid optical element and the rigid optical element also acts as a Media Insert providing energy and functionality to the resulting ophthalmic lens.

Some additional embodiments include a Data Processor 111 placed within a media insert that includes a rigid or formable lens insert fully encapsulated within a hydrogel matrix. A rigid or formable lens insert may be manufactured, for example using microinjection molding technology.

Microinjection molding embodiments can include, for example, a poly(4-methylpent-1-ene copolymer resin with a diameter of between about 6 mm to 10 mm and a front surface radius of between about 6 mm and 10 mm and a rear surface radius of between about 6 mm and 10 mm and a center thickness of between about 0.050 mm and 0.5 mm. Some exemplary embodiments include an insert with diameter of about 8.9 mm and a front surface radius of about 7.9 mm and a rear surface radius of about 7.8 mm and a center thickness of about 0.100 mm and an edge profile of about 0.050 mm radius. One exemplary micromolding machine can include the Microsystem 50 five-ton system offered by Battenfield Inc.

The Data Processor 111 placed upon or within a media insert can be placed in a mold part 101-102 utilized to form an ophthalmic lens. Mold part 101-102 material can include, for example: a polyolefin of one or more of: polypropylene, polystyrene, polyethylene, polymethyl methacrylate, and modified polyolefins. Other molds can include a ceramic or metallic material.

A preferred alicyclic co-polymer contains two different alicyclic polymers and is sold by Zeon Chemicals L.P. under the trade name ZEONOR. There are several different grades of ZEONOR. Various grades may have glass transition temperatures ranging from 105° C. to 160° C. A specifically preferred material is ZEONOR 1060R.

Other mold materials that may be combined with one or more additives to form an ophthalmic lens mold include, for example, Zieglar-Natta polypropylene resins (sometimes referred to as znPP). On exemplary Zieglar-Natta polypropylene resin is available under the name PP 9544 MED. PP 9544 MED is a clarified random copolymer for clean molding as per FDA regulation 21 CFR (c) 3.2 made available by ExxonMobile Chemical Company. PP 9544 MED is a random copolymer (znPP) with ethylene group (hereinafter 9544 MED). Other exemplary Zieglar-Natta polypropylene resins include: Atofina Polypropylene 3761 and Atofina Polypropylene 3620WZ.

Still further, in some embodiments, the molds of the invention may contain polymers such as polypropylene, polyethylene, polystyrene, polymethyl methacrylate, modified polyolefins containing an alicyclic moiety in the main chain and cyclic polyolefins. This blend can be used on either or both mold halves, where it is preferred that this blend is used on the back curve and the front curve consists of the alicyclic co-polymers.

In some preferred methods of making molds 100 according to the present invention, injection molding is utilized according to known techniques, however, embodiments can also include molds fashioned by other techniques including, for example: lathing, diamond turning, or laser cutting.

Typically, lenses are formed on at least one surface of both mold parts 101-102. However, in some embodiments, one surface of a lens may be formed from a mold part 101-102 and another surface of a lens can be formed using a lathing method, or other methods.

Lenses

Figure 2:
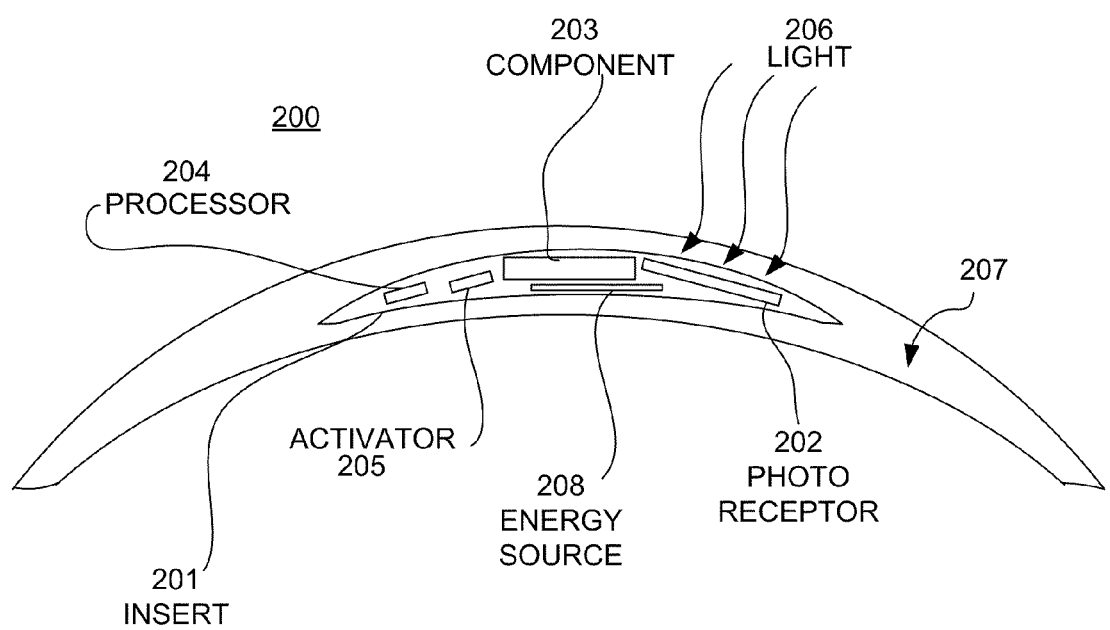
FIG. 2 illustrates aspects of an ophthalmic lens with a media insert including a data processor.

Referring now to FIG. 2 elements of an activated ophthalmic lens 200 with a media insert 201 including a Data Processor 204 are illustrated. As illustrated, the media insert 201 is embedded within a hydrogel lens material 207. An activator 205 can be used to implement one or more executable programs included within a memory storage in the processor 204. In some embodiments, a program executed via the processor 204 can cause a change of state in a component 203. The memory storage can include a random access memory semiconductor; a read only memory semiconductor; a static memory; an erasable programmable read only memory; or other component capable of storing digital data and providing the data on command.

An energy harvester, such as a photoreceptor 202 can be included for recharging an energy source 208, such as a lithium based battery or a capacitor. The data Processor 204 can be used to manage a re-energizing process. For example, the processor can receive data indicative of an amount of charge present in an energy source 208 and open a circuit allowing current to flow from an energy harvester 202 to the energy source 208. In another aspect, the processor can also be programmed to monitor when the energy harvester 202 is capable of providing sufficient current to charge an energy source 208 and provide an electrical pathway via circuitry suitable for such charging. Electrical circuitry for charging can include, for example, transistors acting as switches and diodes for ensuring a proper direction of current flow.

Figure 7:
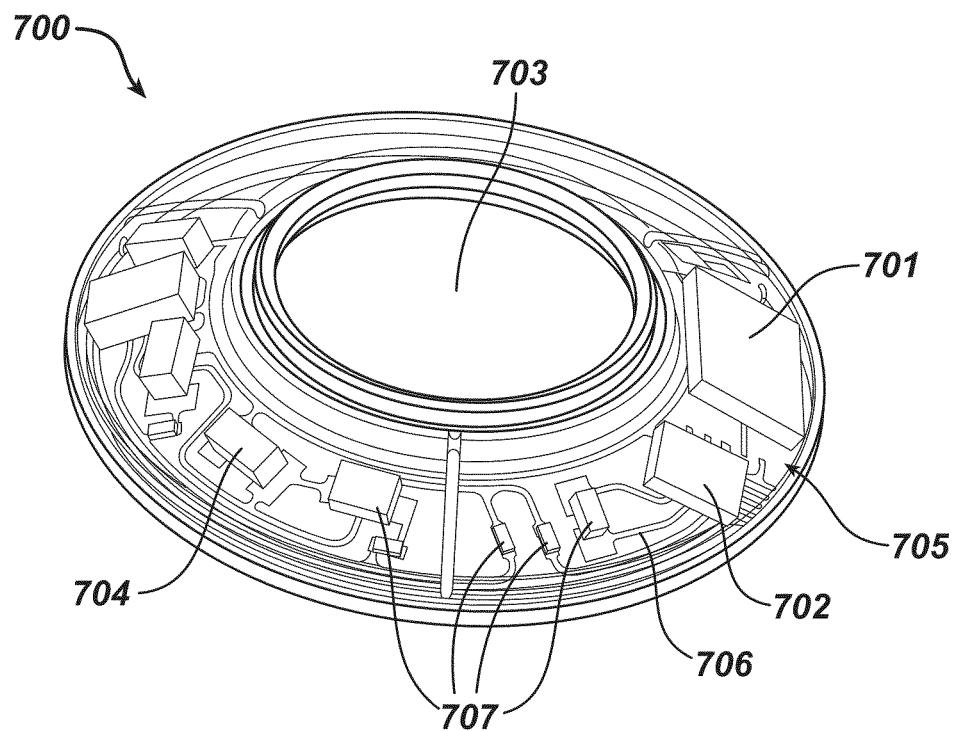
FIG. 7 illustrates a perspective view of some embodiments of an ophthalmic lens including a processor and components.

Referring now to FIG. 7, a perspective view of some embodiments of the present invention is provided. This view illustrates an embodiment of an energy harvester 701 and an energy source 702, each in electrical communication via conductive circuit paths 706 with a data processor 704. Other components 707 can be various semiconductor, solid state, active or passive devices which may play a part in a circuit included in a media insert. In some embodiments, the circuit paths 706, components 707, energy harvester 701, energy source 702 and data processor 704, sensors and other devices may be mounted on a flexible substrate 705.

FIG. 7 additionally illustrates a liquid meniscus lens portion located within an optic zone on the media insert 703.

In some embodiments, a preferred lens material includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Suitable silicone containing components include compounds of Formula I

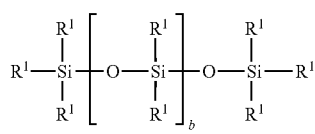

where
$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_i$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present invention will be made from a reactive mixture comprising at least about 20% wt and preferably between about 20% wt and 70% wt silicone containing components based on total weight of reactive monomer components from which the polymer is made.

In another embodiment, one to four $R^1$ comprises a vinyl carbonate or carbamate of the formula:

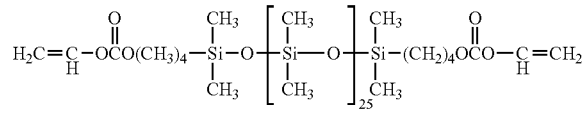

Formula II wherein: Y denotes —O—, —S— or —NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio)propyl-[tris (trimethylsiloxy)silane]; 3-[tris (trimethylsiloxy)silyl] propyl allyl carbamate; 3-[tris (trimethylsiloxy)silyl] propyl vinyl carbamate; trimethylsilylethyl vinyl carbonate; trimethylsilylmethyl vinyl carbonate, and

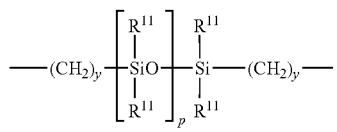

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

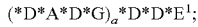

(*D*A*D*G)$_a$*D*D*E$^1$;

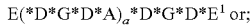

E(*D*G*D*A)$_a$*D*G*D*E$^1$ or;

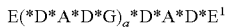

E(*D*A*D*G)$_a$*D*A*D*E$^1$     Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$_a$ is at least 1;
A denotes a divalent polymeric radical of formula:

Formula VII

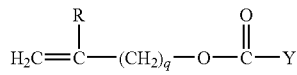

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII

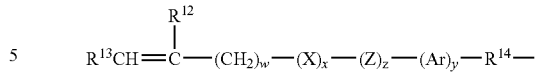

wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

Processes

The following method steps are provided as examples of processes that may be implemented according to some aspects of the present invention. It should be understood that the order in which the method steps are presented is not meant to be limiting and other orders may be used to implement the invention. In addition, not all of the steps are required to implement the present invention and additional steps may be included in various embodiments of the present invention.

Figure 4:
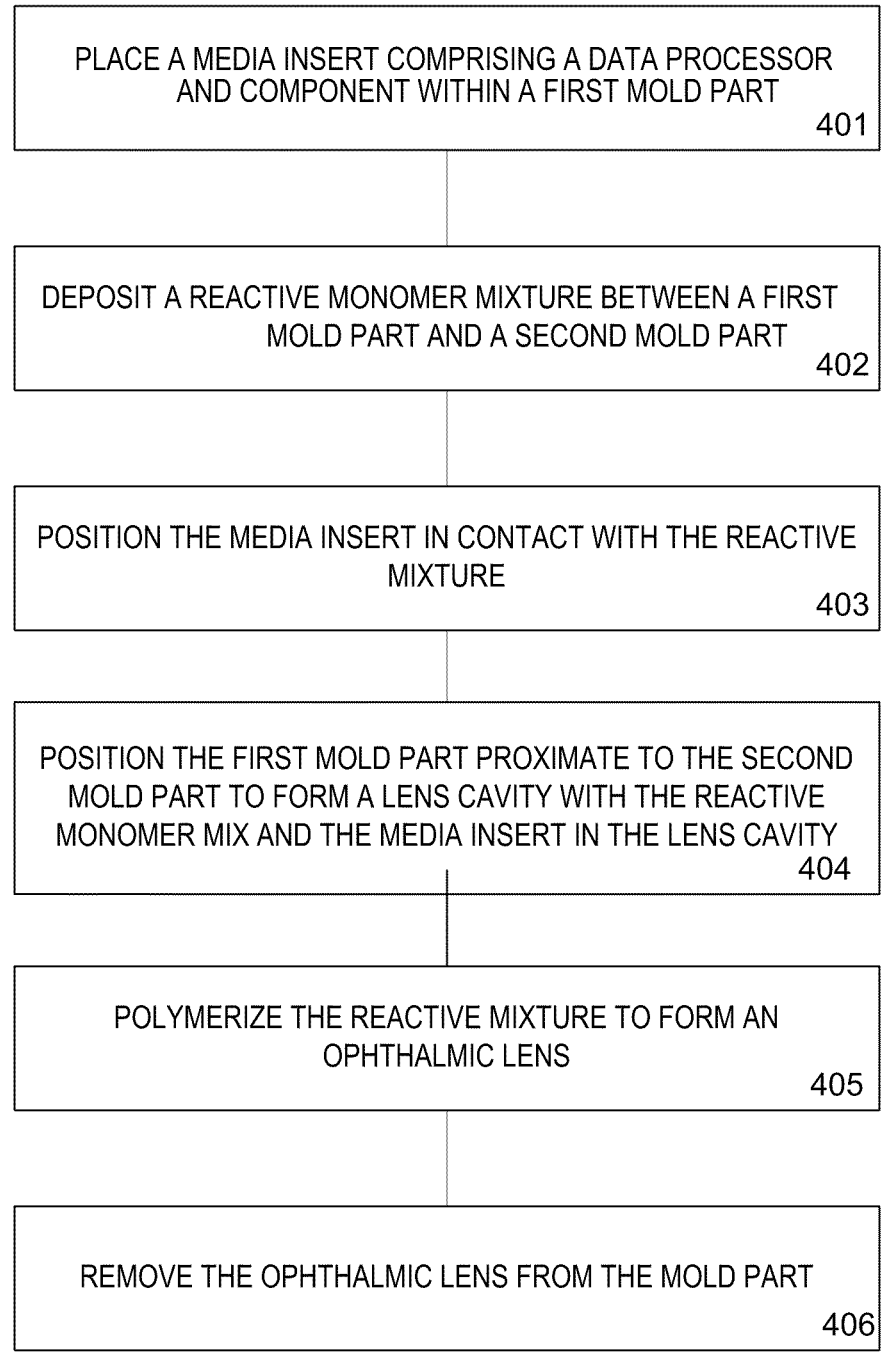
FIG. 4 illustrates method steps according to some embodiments of the present invention.

Referring now to FIG. 4, a flowchart illustrates exemplary steps that may be used to implement the present invention. At 401, a Data Processor is placed within a mold part. In some embodiments, the Data Processor may be included with a media insert. The media insert may be rigid or flexible. A media insert may or may not also contain one or more components.

At 402, a reactive monomer mix can be deposited into a mold part.

At 403, the Data Processor 111 is placed into the mold part. In some preferred embodiments, the Data Processor 111 is placed in the mold part via mechanical placement. Mechanical placement can include, for example, a robot or other automation, such as those known in the industry to place surface mount components. Human placement of a Data Processor is also within the scope of the present invention. Accordingly, any mechanical placement effective to place a Data Processor with an Energy Source within a cast mold part such that the polymerization of a Reactive Mixture contained by the mold part will include the variable optic in a resultant ophthalmic lens.

In some embodiments, a processor device, MEMS, NEMS or other component may also be placed into the Data Processor and in electrical contact with the Energy Source.

At 404, the first mold part can be placed proximate to the second mold part to form a lens forming cavity with at least some of the reactive monomer mix and the Energy Source in the cavity. At 405, the reactive monomer mix within the cavity can be polymerized. Polymerization can be accomplished, for example, via exposure to one or both of actinic radiation and heat. At 406, the lens is removed from the mold parts.

Although invention may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Referring now again to FIG. 4, at 403, a reactive mixture is placed between a first mold part and a second mold part in contact with the Data Processor. At 404 the first mold part is positioned proximate to the second mold part to form a lens cavity with the reactive monomer mix and the variable lens in the lens cavity.

At 405, the reactive mixture is polymerized, such as for example via exposure to one or both of actinic radiation and heat. At 406, an ophthalmic device incorporating the data processor is removed from the mold parts.

Referring now to FIG. 5 at 501, a Data Processor is placed within an ophthalmic lens, as discussed above. At 502, the Data Processor is placed in electrical communication with an Energy Source. Electrical communication can be accomplished, for example, via circuitry incorporated into the data processor or via pathways ink jetted or otherwise formed directly upon lens material.

At 503, electrical energy is directed through the data processor incorporated into the ophthalmic lens. The energy can be directed, for example, via electrical circuitry capable of conducting the electrical charge. At 504 the variable optic changes at least one optical quality of the lens.

Apparatus

Figure 3:
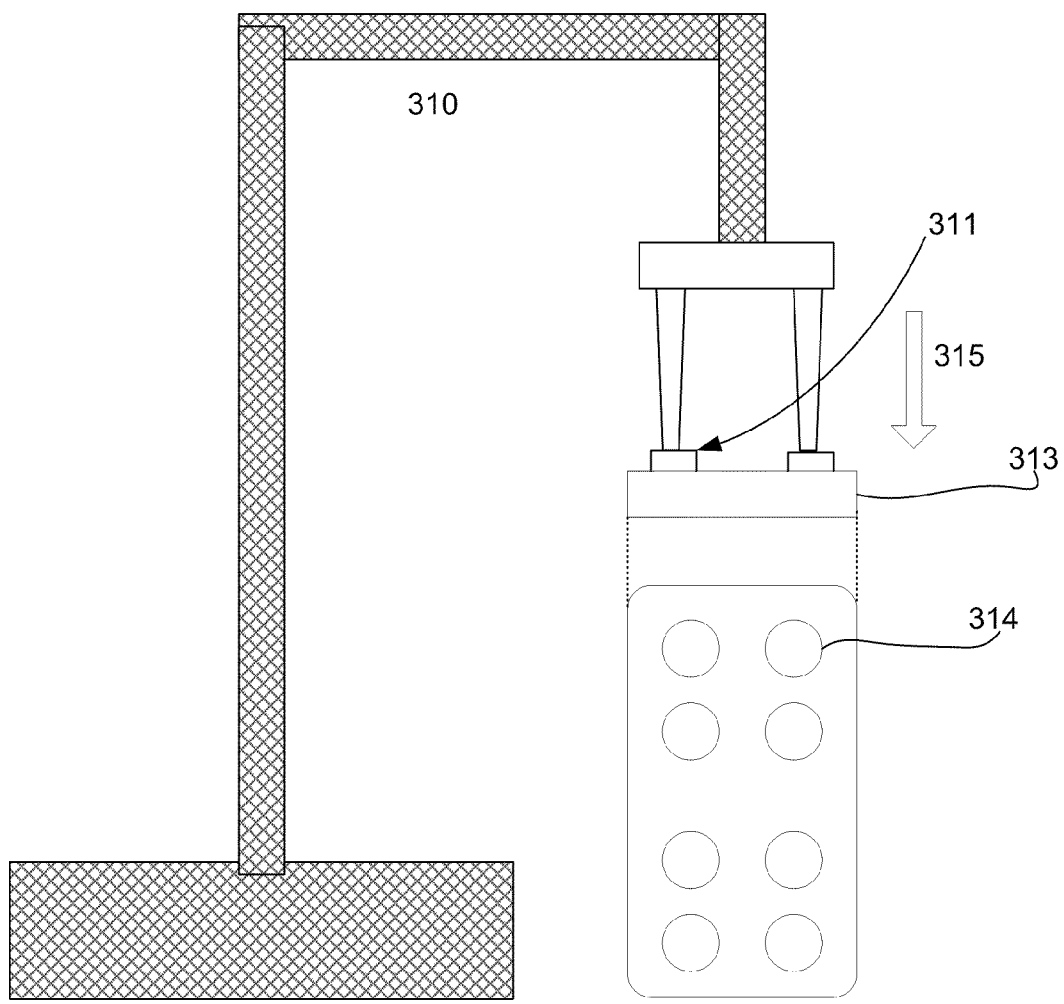
FIG. 3 illustrates an apparatus for placing media insert including a data processor within an ophthalmic lens mold part.

Referring now to FIG. 3, automated apparatus 310 is illustrated with one or more transfer interfaces 311. As illustrated, multiple mold parts are each associated a mold part receptacle 314 contained within a pallet 313 and presented to a transfer interface 311. The transfer interface 311 will place a processor or an insert containing a processor within a mold part 314 used to form an ophthalmic lens. Embodiments can include a single interface individually placing a data processor, or multiple interfaces (not shown) simultaneously placing processors within multiple mold parts, and in some embodiments, in each mold part.

Another aspect of some embodiments includes apparatus to support the media insert including a data processor while the body of the ophthalmic lens is molded around these components. In some embodiments an Energy Source may affixed to holding points in a lens mold (not illustrated). The holding points may be affixed with polymerized material of the same type that will be formed into the lens body.

Figure 6:
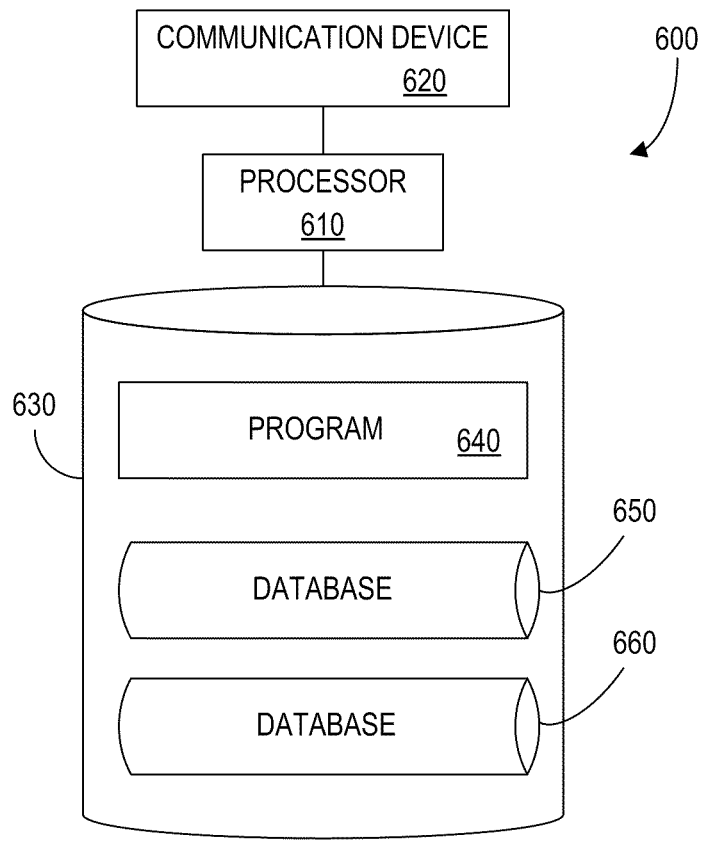
FIG. 6 illustrates a processor that may be used to implement some embodiments of the present invention.

Referring now to FIG. 6 a controller 600 is illustrated that may be used in some embodiments of the present invention. The controller 600 includes a processor 610, which may include one or more processor components coupled to a communication device 620. In some embodiments, a controller 600 can be used to transmit energy to the Energy Source placed in the ophthalmic lens.

The controller can include one or more processors, coupled to a communication device configured to communicate energy via a communication channel. The communication device may be used to electronically control one or more of: the placement of a variable optic insert into the ophthalmic lens and the transfer of command to operate the variable optic device.

The communication device 620 may also be used to communicate, for example, with one or more controller apparatus or manufacturing equipment components.

The processor 610 is also in communication with a storage device 630. The storage device 630 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 630 can store a program 640 for controlling the processor 610. The processor 610 performs instructions of the program 640, and thereby operates in accordance with the present invention. For example, the processor 610 may receive information descriptive of variable optic insert placement, processing device placement, and the like. The storage device 630 can also store ophthalmic related data in one or more databases. The database may include customized Media Insert designs, metrology data, and specific control sequences for controlling energy to and from a Media Insert.

CONCLUSION

The present invention, as described above and as further defined by the claims below, provides methods of providing an Energized Lens with a Data Processor and apparatus for implementing such methods, as well as ophthalmic lenses formed with a Data Processor therein.

The invention claimed is:

1. A method of forming a contact lens, the method comprising the steps of:
   forming a media insert by attaching a data processor, a battery and a liquid meniscus lens to a substrate;
   positioning the media insert within a portion of a contact lens mold;
   depositing a reactive monomer mix into the contact lens mold and encapsulating the media insert therein; and
   exposing the reactive monomer mix to actinic radiation or heat to form the contact lens.

2. The method of forming a contact lens of claim 1, wherein the step of forming the media insert further comprises attaching an energy harvester to the substrate.

3. The method of forming a contact lens of claim 2, wherein the energy harvester comprises a photoreceptor.

4. The method of forming a contact lens of claim 1, wherein the step of forming the media insert further comprises forming a conductive circuit path on the substrate between the data processor and the battery.

5. The method of claim 1, wherein the step of forming the media insert further comprises attaching a focus adjustment activator selected from the group consisting of a magnetically activated switch, a photo-optically activated switch, and an electrical sensor configured to sense a signal within an eye to the substrate in communication with said data processor.

6. The method of claim 1, wherein said substrate is flexible.

\* \* \* \* \*